United States Patent [19]  [11] 4,088,538
Schneider  [45] May 9, 1978

[54] REVERSIBLY PRECIPITABLE IMMOBILIZED ENZYME COMPLEX AND A METHOD FOR ITS USE

[75] Inventor: Michel Schneider, Grand-Lancy, Switzerland

[73] Assignee: Battelle Memorial Institute, Switzerland

[21] Appl. No.: 690,096

[22] Filed: May 26, 1976

[30] Foreign Application Priority Data

May 30, 1975 Switzerland .................. 6965/75

[51] Int. Cl.$^2$ .................. C07G 7/02; C08F 216/34; C08F 220/06; C12D 13/02
[52] U.S. Cl. .................. 195/63; 195/31 R; 195/31 F; 195/68; 195/116; 195/DIG. 11
[58] Field of Search .................. 195/31 R, 31 F, 68, 195/63, 65, 116, 115, DIG. 11

[56] References Cited

U.S. PATENT DOCUMENTS

| 3,576,760 | 4/1971 | Gould et al. | 195/68 X |
| 3,625,827 | 12/1971 | Wildi et al. | 195/63 |
| 3,649,457 | 3/1972 | Westman | 195/68 |
| 3,654,083 | 4/1972 | Moelker | 195/68 |
| 3,695,999 | 10/1972 | Fogione et al. | 195/63 |
| 4,017,364 | 4/1977 | Van Leemputten | 195/68 |

FOREIGN PATENT DOCUMENTS

| 2,423,059 | 8/1975 | Germany | 195/68 |
| 1,353,317 | 5/1974 | United Kingdom | 195/63 |

*Primary Examiner*—Alvin E. Tanenholtz
*Assistant Examiner*—Thomas G. Wiseman
*Attorney, Agent, or Firm*—Robert E. Burns; Emmanuel J. Lobato; Bruce L. Adams

[57] ABSTRACT

A process for using and preparing a reversibly soluble enzymatically active polymer enzyme product which consists of an enzyme covalently bonded to a water soluble organic polymer selected from polyacrylic acid, dextran, carboxy methyl cellulose, and polyethylene glycol which have carboxyl or amino side groups that impart to the complex its reversible solubility.

10 Claims, No Drawings

REVERSIBLY PRECIPITABLE IMMOBILIZED ENZYME COMPLEX AND A METHOD FOR ITS USE

The object of the present invention is a process for the use of an enzyme in order, by enzymatic reaction, to transform an organic substance into at least one different organic substance, in which the enzyme is attached, by covalent bonds, onto an organic polymer which is soluble in aqueous medium, so as to form an active enzymatic complex which is soluble in aqueous medium, and the complex is maintained, in dissolved state, in an aqueous solution of the substance to be transformed, for a period of time and at a temperature sufficient to permit the obtaining of the desired degree of transformation of said substance.

The use of enzymes in order to transform an organic substance into at least one other organic substance is well known in industry, particularly in the food industry.

The traditional processes for the use of enzymes to effect an enzymatic reaction consist in introducing the enzyme, in dissolved state, into a reaction medium, generally a liquid, which contains the substance (so-called "substrate") which it is desired to transform, and maintaining said reaction medium at a temperature and for a period of time sufficient to permit the obtaining of the desired degree of transformation of said substance.

Upon the carrying out of these processes, it is not possible, at the end of the reaction, to recover the excess, if any, of unconsumed enzyme. For this reason the remaining amount of enzyme is generally destroyed in situ in order to avoid the presence of enzyme in mixture with the reaction product.

On the other hand, since the cost of enzymes is generally high, it is possible in practice, for reasons of an economic nature, to use only small quantities thereof, which results in a low enzymatic reaction velocity, which velocity in most cases is insufficient to permit the use of enzymes of an industrial scale. It is only in the case of enzymes which are of relative low price, such as the proteases and amylases, that industrial utilization of these processes can be contemplated.

In accordance with more recent processes, use is made of "immobilized enzymes", that is to say enzymes which are fixed by covalent bonds on a suitable organic polymer, so as to constitute an active enzymatic complex.

These last mentioned processes make it possible to recover any excess of enzyme after the enzymatic reaction. These processes therefore make it possible to use a larger amount of enzyme than the amount theoretically necessary for the transformation of the substance subjected to the enzymatic reaction, which results in an increase in the velocity of this reaction and therefore in the hourly yield.

Moreover, the attaching of an enzyme to a polymer, in the form of an active enzymatic complex, generally has the effect of increasing the stability of the enzyme and, on the other hand, in certain cases makes it possible to increase the useful pH range of the reaction medium and facilitate the adjustment of the course of the enzymatic reaction.

Finally, the use of an enzyme in "immobilized" state in the form of an active enzymatic complex makes it possible to obtain the product of the enzymatic reaction directly in a state which is free of enzyme.

The enzyme may be attached either to a water-insoluble polymer so as to form an active enzymatic complex in solid state which is insoluble in aqueous medium, or to a water-soluble polymer so as to form an active enzymatic complex which is soluble in aqueous medium.

In the former case, the insoluble active enzymatic complex can be used in the form of particles of powder in a column similar to solid-phase chromatography columns through which the reaction medium is passed, or else in suspension in a vessel containing the reaction medium.

Due to the fact that the active enzymatic complex is in solid state in the reaction medium, this complex can easily be separated inexpensively from the reaction medium and recovered at the end of the enzymatic reaction.

However, this manner of procedure, when a column is used, has the drawback of the danger of the clogging of the column or of the production of so-called "channeling" (flow of the reaction medium in the form of liquid streams which are limited to only a portion of the cross section of the column).

When the enzymatic reaction is carried out in a tank, the use of a solid active enzymatic complex has the drawback of poor efficiency of contact between the particles of said complex and the substance which it is desired to transform, due to the difficulty, or impossibility, of said medium penetrating into these particles.

The use of an active enzymatic complex dissolved in the reaction medium makes it possible to carry out the enzymatic reaction in a homogeneous liquid medium, which improves the effectivensss of the contact between the enzymatic complex and the substance to be transformed and therefore increases the yield of the reaction.

Moreover, the percentage attachment of the enzyme to an organic polymer which is soluble in aqueous medium is generally greater than that of the attachment of this same enzyme to an insoluble organic polymer. Moreover, the use of a polymer which is soluble in aqueous medium in order to attach the enzyme makes it possible to obtain an enzymatic complex whose specific activity, expressed in units of enzyme per units of mass of the complex is generally higher than that of the enzymatic complexes obtained by attaching the enzyme to an insoluble polymer.

(An enzyme unit is defined as the quantity of enzyme which makes it possible to cause the complete transformation of one micromol of substrate per minute under optimum reaction conditions.)

On the other hand, for given operating conditions, the activity of an enzyme with respect to a substrate of high molecular weight is generally greater when said enzyme is attached to a polymer which is soluble in the reaction medium than when said enzyme is attached to an insoluble polymer. The use of an active enzymatic complex in solution in the reaction medium also has the advantage over the use of an insoluble solid active enzymatic complex that it makes it possible to avoid the proliferation of micro-organisms, which frequently takes place in the case of the solid enzymatic complexes. For this purpose, it is sufficient to effect a filtration of the solution of soluble enzymatic complex through a microfilter, for instance a filter having pore sizes of the order of 0.2 microns, so as to retain the microorganisms and obtain a sterile solution of active enzymatic complex as filtrate.

However, the use of the active enzymatic complexes soluble in aqueous medium which have been proposed up to the present time presents the drawback that an ultra-filtration of the reaction medium is required in order to separate the reaction product from the enzymatic complex and to recover the latter for its further reuse. Such ultra-filtration requires the use of costly equipment and is furthermore a cause of a decrease in the overall yield of the process. This drawback therefore stands in the way of the industrial use of the active enzymatic complexes which are soluble in aqueous medium.

The object of the present invention is to combine the advantages of the use of an insoluble active enzymatic complex with those of the use of a soluble enzymatic complex, without having the drawbacks thereof.

For this purpose, the process of the invention is characterized by the fact that the organic polymer is selected from polymers which form an active enzymatic complex which is reversibly precipitable and retains its enzymatic activity after redissolving, and that, after the desired degree of transformation of the substance to be transformed has been obtained, the enzymatic complex is precipitated and removed from the reaction medium.

In the present specification the expression "reversibly precipitable" means that the enzymatic complex is capable of being redissolved after it has been precipitated, and that it can be again precipitated from the solution thus obtained, which successive precipitating and redissolving operations can be repeated an indefinite number of times, without change in the physical-chemical and enzymatic properties of the complex, either in dissolved state or in the state of a precipitate.

It should be noted that the phenomena which may be involved in the precipitation and redissolving of the enzymatic complex are not necessarily "reversible" in a thermodynamic sense of the term, that is to say they do not exclude heat exchanges with the outside environment.

As water-soluble organic polymer one can use, for instance, a derivative of polyacrylic acid, such as polyacrylomide or else a dextran, carboxymethylcellulose, polyethyleneglycol, etc., this polymer having chemical groups which impart to it the property of reversibly precipitating or flocculating in aqueous medium as a result of a modification of at least one physicochemical parameter of said medium, such as the temperature, pH, concentration of solute, etc., or else by adding to such medium ions, such as bivalent or trivalent metallic ions, which are capable of bringing about the precipitation of the enzymatic complex, combined with the further use of at least one complexing agent for said ions in order to cause the redissolving of the active enzymatic complex.

In particular, as organic polymer one can employ a derivative of polyacrylamide bearing —COOH side groups which impart to it the property of precipitating quantitatively and reversibly by decrease of the pH of the medium below a value of the order of 4.5 to 5, while being soluble in this same medium at a pH higher than this value.

More particularly, one can employ organic polymers having acid side groups of the benzoic or isophthalic type. Such polymers have the advantage that they are precipitable at a pH of less than 4.5 in a manner which is practically quantitative since the proportion of complex remaining in solution after the precipitation is generally less than 1 ppm referred to the initial quantity.

Example 1

A. Preparation of the active enzymatic complex:

Acrylic chloride and p-amino benzoic acid are reacted in accordance with the equation:

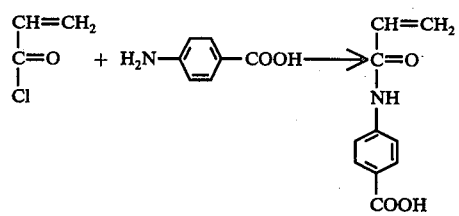

whereupon the monomer thus obtained is polymerized in aqueous medium in a nitrogen atmosphere and in the presence of a small amount of N,N'-methylene-bis-acrylamide and of ammonium persulfate, the latter compound serving as polymerization catalyst.

In this way there is obtained a water-soluble polymer derived from polyacrylamide, composed of interconnected macromolecular linear chains having the recurrent unit:

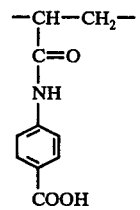

An aqueous solution of this polymer is filtered by passing it through a filter having pores of 0.22 microns, whereupon the polymer is precipitated in the filtrate by lowering the pH to 4.5 by means of a dilute aqueous solution of citric acid. Thereupon the precipitate is collected and dried.

Molecules of glucose isomerase are attached to this polymer by proceeding in the following manner:

the polymer precipitate obtained in the manner described above is placed in suspension in dioxan (in a proportion of 10 ml of dioxan per g of precipitate) whereupon 1.1 ml of n-tributylamine per 10 ml of the suspension is added;

the suspension is cooled to 0° C and 0.4 ml of ethyl chloroformate is added;

the suspension is maintained at 0° C for 10 minutes whereupon 10 ml of aqueous glucose isomerase solution (20 g/liter) is added for every 10 ml of the suspension;

the mixture which has thus been formed is maintained for 15 minutes at 0° C, evaporated to dryness, and the solid residue obtained is dissolved in water;

the enzymatic complex thus obtained is precipitated by lowering the pH to 4.5 by means of a dilute aqueous solution of citric acid;

the precipitate is washed with an aqueous solution of sodium chloride (0.1 M) until no further enzymatic activity appears in the liquid, whereupon it is subjected to a final washing with distilled water and dried.

In this way one obtains an enzymatic complex which is soluble in water (at a pH of more than 4.5) and has an enzymatic activity corresponding to 1500 enzyme units per g of complex (an enzyme unit being defined by the amount of fructose, expressed in micromols, produced in 30 minutes, at 50° C, from an 0.66 M glucose solution containing this enzymatic complex in solution.

B. Use of the enzymatic complex to effect the transformation of glucose into fructose:

Reaction medium: 250 ml of an aqueous glucose solution of 12% by weight.
Reaction temperature: 50° C.
pH of the reaction mixture during the enzymatic reaction: 7.0.

Two tests are carried out, one using 0.18 g of active enzymatic complex and the other using 1 g thereof (the complex having been previously dissolved in a small amount of water).

The partial transformation of glucose into fructose (51% by weight fructose; 49% by weight glucose) is obtained at the end of a time of reaction of 40 hours when using 0.18 g of enzymatic complex and 9 hours when using 1 g of enzymatic complex.

After reaction, the enzymatic complex is precipitated by lowering the pH of the reaction medium to 4.5 by means of an aqueous solution of citric acid, whereupon this precipitate is separated from the reaction medium by settling.

This precipitate is then washed with an aqueous solution of citric acid having a pH of 4.5 and then dissolved in water; the resultant solution is filtered through a filter having pores of 0.22 microns and the enzymatic complex is precipitated by lowering the pH to 4.5, whereupon finally it is dried.

The powdered enzymatic complex thus obtained is ready to be used again in the same manner as just described, with its enzymatic activity unchanged.

EXAMPLE 2

The same procedure is employed as in Example 1 but instead of causing the precipitation of the enzymatic complex after the reaction by lowering the pH of the reaction medium to 4.5, this precipitation is produced by adding to the medium 2 ml of a 1M solution of calcium chloride, CaCl$_2$, of a pH of 7.0, the pH of the reaction medium being maintained at a value of 7.0.

One thus obtains the precipitation of 98% of the active enzymatic complex.

The precipitate thus obtained is separated from the reaction medium by centrifuging, whereupon it is introduced into an aqueous solution of ethylenediamine tetraacetic acid (E.D.T.A., a well-known complexing agent for calcium ions). The redissolving of the active enzymatic complex is thus effected and the E.D.T.A./calcium complex is separated from the aqueous redissolving medium by dialysis. The aqueous solution of enzymatic complex which is free of calcium ions which has thus been obtained and which has the same enzymatic activity as it initially had can be reused for a new operation of transforming glucose into fructose, as described in Example 1.

EXAMPLE 3

The same procedure is employed as in Examples 1 and 2, except that the precipitation of the enzymatic complex after the reaction is brought about by the simultaneous addition to the reaction medium of 2 ml of a 1M solution of calcium chloride with a pH of 7.0 and of 50 ml of ethanol, the pH of the reaction medium being maintained at 7.0. In this way 99.7% of the active enzymatic complex is precipitated.

EXAMPLE 4

A. Preparation of the active enzymatic complex

A methyl ester of polyacrylic acid formed of linear macromolecules having the recurrent unit:

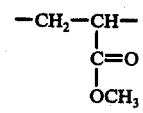

and having a molecular weight of 80,000 is reacted with hydrazine at 90° C so as to form a polyacrylamide hydrazide (polymer formed of linear macromolecules having the recurrent unit:

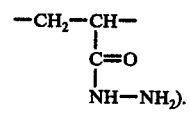

The polyacrylamide hydrazide is then transformed into the corresponding azide derivative by reaction at 0° C in the presence of a mixture of hydrochloric acid and sodium nitride, in accordance with the reaction:

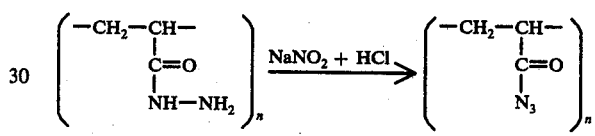

in which $n$ represents the number of recurrent units per molecule of macromolecular substance.

Thereupon, glucoamylase molecules are attached to the polymer thus obtained by reacting said enzyme with this polymer at 0° C in an aqueous medium having a pH of 9.4.

In this way, an active enzymatic complex is obtained dissolved in aqueous medium which however does not have the property of being reversibly precipitatable which is required for the enzymatic complexes which enter into consideration for the carrying out of the invention. In order to obtain a soluble, reversibly precipitable enzymatic complex, the copolymer is formed between the nonprecipitable soluble complex obtained in the manner just described and the monomer derived from acrylamide having the formula

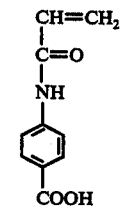

prepared in the manner described in Example 1.

For this purpose, an aqueous solution is prepared which contains, in mixture, this complex and this monomer in dissolved state, and the monomer is polymerized in this solution in the presence of ammonium persulfate, in a nitrogen atmosphere.

In this way there is obtained an active enzymatic complex which is soluble in water at a pH of more than 4.5 and reversibly precipitable at a pH of less than 4.5 and which has an enzymatic activity corresponding to 4800 enzyme units per gram (one enzyme unit corresponding to the amount of glucose, expressed in micromols, produced in one minute at 60° C from an aqueous solution of enzymatically "liquified" starch containing 30% by weight solids (commercial product sold by the A.E. Staley Manufacturing Co.).

B. Use of the enzymatic complex to effect the transformation of starch into glucose:

To 250 ml of an aqueous solution of "liquified" starch containing 30% by weight solids, maintained at 60° C and the pH of which is brought to 5, there are added 2 g of the soluble, precipitatable active enzymatic complex the preparation of which has been described above, and the reaction medium thus formed is maintained at 60° C.

At the end of 12 hours the starch is practically entirely transformed into glucose. The reaction medium is then allowed to cool to room temperature whereupon its pH is lowered to 4.5 so as to cause the precipitation of the enzymatic complex, and the latter is removed from the reaction mixture by centrifuging.

The enzymatic complex thus recovered may be re-used repeatedly in the same manner as just described, it exhibiting just as high an enzymatic activity as upon its initial use.

EXAMPLE 5

A. Preparation of the active enzymatic complex:

Proceeding in the manner described in Example 4, the azide derivative of polyacrylamide hydrazide is prepared, whereupon molecules of glucose isomerase are attached to this polymer derivative, proceeding in the manner described in Example 4, in the case of the attachment of glucoamylase to this same polymer. In this way an enzymatic complex is obtained.

On the other hand, an acrylic monomer of the formula

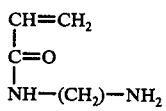

is prepared by reaction between acrylyl chloride and ethylene diamine.

The monomer thus obtained is mixed in aqueous solution with the said enzymatic complex of glucose isomerase and the polymerization of said monomer is effected in said solution in a nitrogen atmosphere in the presence of ammonium persulfate.

In this way there is obtained an enzymatic complex which comprises glucose isomerase molecules attached via their amino groups, -to an acrylic copolymer having side chains terminated by amino groups.

This last-mentioned enzymatic complex is an amphoteric polymer which is soluble in aqueous medium but precipitated by bringing the pH of this medium to 7.6 (isoelectric point of this complex).

B. Use of enzymatic complex to effect the transformation of glucose into fructose:

The same procedure is used as in Example 1, except that the precipitation of the enzymatic complex after the reaction is brought about by bringing the pH of the reaction medium to a value of 7.6.

EXAMPLE 6

A. Preparation of the active enzymatic complex:

Carboxymethylcellulose hydrazide is transformed into the corresponding azide derivative by reaction at 0° C in the presence of sodium nitrite and hydrochloric acid, whereupon the azide thus formed is reacted, still at 0° C, in an aqueous medium of a pH of 8.7 with a mixture of orthoaminobenzoic acid and lactose (Miles). For 1 g of initial hydrazide derivative 0.5 g of lactase and 0.2 g of orthoaminobenzoic acid are used.

In this way there is obtained an active enzymatic complex which is soluble in water with a pH of more than 4.5 and reversibly precipitable at a pH of less than 4.5, formed of a polyanhydroglucose macromolecular chain bearing side groups derived from orthoaminobenzoic acid and other side groups formed of lactase molecules, all these groups being bound to the polyanhydroglucose chain by groups of the formula: —O—CH$_2$—CO—NH—.

This enzymatic complex has an enzyme activity corresponding to 520 units of lactase per gram.

B. Use of the enzymatic complex to effect the transformation of lactose into galactose and glucose:

To 250 ml of an aqueous solution containing 5% by weight lactose, of a pH of 6.6, which is maintained at 40° C there is added 1 g of the enzymatic complex obtained in the manner described above.

The enzymatic reaction is allowed to proceed for 2 hours, whereupon the enzymatic complex is precipitated by lowering the pH of the reaction medium to 4.5 by a dilute solution of citric acid. The precipitate thus obtained is separated by settling, from the reaction medium. The enzymatic complex thus recovered can be used again several times, after purification by redissolving in aqueous medium at a pH of 7.0 and filtering through a filter having, for instance, pores of 0.22 microns, without losing its original enzymatic activity.

The analysis of the reaction medium after separation of the enzymatic complex indicates that 30% of the initial quantity of lactose has been converted into galactose and glucose.

The method which has just been described is capable of very different industrial applications, in particular in the following fields:

Utilization of lactose serum by hydrolysis of the lactose.

Isomerization of glucose by means of glucose isomerase in order to obtain glucose and fructose syrup of high sweetening power.

Production of invert sugar from sucrose, by means of invertase.

Degradation of starch into glucose by means of alphaamylase and amyloglucosidase.

Production of maltose from starch by means of betaamylase and amyloglucosidase.

Production of highly fermentable syrups for the beer manufacturing industry.

I claim:

1. A process for the enzymatic processing of a substrate which is subject to enzymatic action using a reversibly precipitable enzymatically active polymer-enzyme product, said product being an enzyme covalently bound to a water-soluble organic polymer selected from the group consisting of polyacrylic acid, water-soluble derivatives thereof, dextran, carboxymethylcellulose and polyethylene glycol and having side groups for reversible flocculation in aqueous media, comprising the steps wherein the said polymer-enzyme product is maintained in dissolved state, in an aqueous solution of the said substrate as reaction medium for a period and at a temperature sufficient to achieve the desired degree of enzymatic reaction, and then precipitating and separating the polymer-enzyme product from the reaction medium.

2. A reversibly precipitable enzymatically active water-soluble polymer-enzyme product wherein the enzyme is covalently bound to a water-soluble organic polymer consisting of macromolecular chains selected from the group consisting of polyacrylic acid, water-soluble derivatives thereof, dextran, carboxymethylcellulose and polyethylene-glycol, said macromolecular chains being covalently bound to side groups which impart to said polymer-enzyme product the property of reversibly precipitating or flocculating in aqueous media as a result of the variation of at least one physicochemical parameter of said medium or by addition of bivalent or trivalene metallic ions to said medium.

3. The product according to claim 2 wherein said polyacrylic acid derivative is a water-soluble polyacrylamide.

4. The product according to claim 2, wherein the side groups which impart to said polymer-enzyme product the property of reversibly precipitating or flocculating in aqueous media are selected from the group consisting of —COOH and —NH$_2$.

5. The product according to claim 4, wherein the —COOH groups are part of a monovalent radical selected from the group consisting of orthobenzoic, parabenzoic and isophthalic radicals.

6. The product according to claim 4, wherein the —NH$_2$ groups are covalently bound to the macromolecular chain through a methylene radical.

7. The product according to claim 2, wherein said metallic ions are selected from the group consisting of bivalent metallic ions.

8. The product according to claim 7, wherein said bivalent metallic ions are calcium ions.

9. The product according to claim 2, wherein the enzyme is selected from the group consisting of glucose isomerase, glucoamylase, lactase, invertase, alpha-amylase and amyloglucosidase.

10. The product according to claim 2, consisting of polyanhydroglucose macromolecular chain bearing side groups derived from orthoaminobenzoic acid and side groups formed of lactase molecules, both type of side groups being bound to the polyanhydroglucose chain by groups of the formula: —O—CH$_2$—CO—NH—.

* * * * *